United States Patent [19]

Beranger et al.

[11] Patent Number: 4,810,706
[45] Date of Patent: Mar. 7, 1989

[54] PIPERAZINE DERIVATIVES OF THEOPHYLLINE AND THEOBROMINE

[75] Inventors: Serge Beranger, Bretigny; J. Claude Pascal, Cachan; Henri Pinhas, Paris; Isabelle Jullien, Bures-sur-Yvette, all of France

[73] Assignee: Recherche Syntex, France

[21] Appl. No.: 811,568

[22] Filed: Dec. 20, 1985

[51] Int. Cl.⁴ .................... C07D 473/08; A61K 31/52
[52] U.S. Cl. .................... 514/265; 544/266; 544/267
[58] Field of Search ............... 544/267, 266; 514/265, 514/262

[56] References Cited

U.S. PATENT DOCUMENTS

| | | | |
|---|---|---|---|
| 4,374,835 | 2/1983 | Favier et al. | 424/250 |
| 4,400,381 | 8/1983 | Favier et al. | 424/248.52 |
| 4,493,837 | 1/1985 | Sugimoto et al. | 544/267 |
| 4,548,820 | 10/1985 | Regnier et al. | 544/267 |
| 4,603,204 | 7/1986 | Thiele et al. | 544/269 |

FOREIGN PATENT DOCUMENTS 0077278 6/1981 Japan .

*Primary Examiner*—Nicholas S. Rizzo
*Attorney, Agent, or Firm*—Brian Lewis; Tom M. Moran; Alan M. Krubiner

[57] ABSTRACT

New compounds of formulas I and II

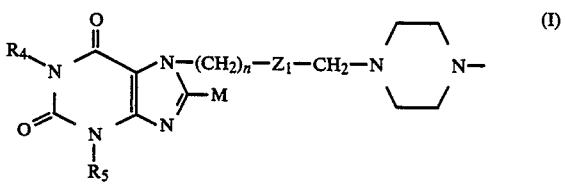

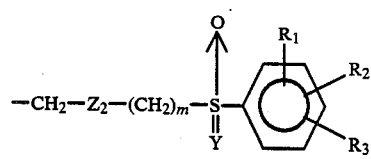

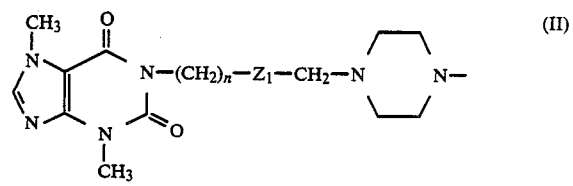

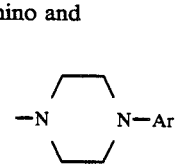

and the pharmaceutically acceptable acid addition salts thereof, wherein M is selected from the group consisting of hydrogen, morpholino, benzylamino, di-n-lower alkylamino, n-lower alkylamino and $$-N\underset{\phantom{xx}}{\overset{\phantom{xx}}{\diagup\!\!\diagdown}}N-Ar$$

wherein Ar is optionally substituted phenyl;
$Z_1$ and $Z_2$ are each independently selected from the group consisting of $CH_2$, CHOB and C=O, wherein B is selected from the group consisting of hydrogen and alkanoyl;
Y is oxygen or nothing;
n is an integer from 0–4 but cannot be zero when $Z_1$ is CHOB;
m is an integer from 0–4 but cannot be zero when $Z_2$ is CHOB;
$R_1$, $R_2$ and $R_3$ are each independently hydrogen, halogen, hydroxy, trifluoromethyl, alkyl or alkoxy;
$R_4$ is lower alkyl; and
$R_5$ is hydrogen or lower alkyl, are antihistamines and are therefore useful in the treatment of respiratory diseases including asthma, hay fever, allergies and the common cold. They are also vasodilators.

3 Claims, No Drawings

PIPERAZINE DERIVATIVES OF THEOPHYLLINE AND THEOBROMINE

BACKGROUND OF THE INVENTION

This invention relates to piperazine derivatives of theophylline and theobromine and to their utility as treatment compounds for respiratory and allergic diseases.

Theophylline and theobromine are well known as diuretics, cardiac stimulants and smooth muscle relaxants. Addition of the piperazine containing substituent confers a range of pharmacologic activities which render the resulting compounds useful in the symptomatic treatment of asthma, hay fever and other respiratory diseases such as, for example, the common cold. The compounds of this invention are sulfur oxidized derivatives and N-demethylated analogs of the piperazine derivatives of theophylline and theobromine which are disclosed in U.S. Pat. Nos. 4,374,835, 4,374,837 and 4,400,381. It has been discovered that the compounds of this invention possess an unexpectedly high degree of antihistaminic activity and prolonged duration of action.

SUMMARY OF THE INVENTION

The present invention concerns novel compounds of formula I and II

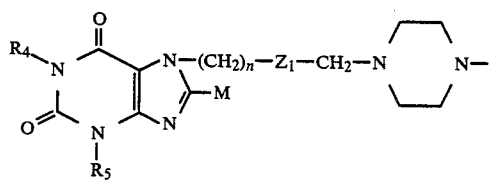
(I)

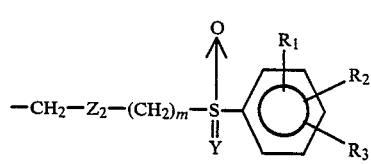

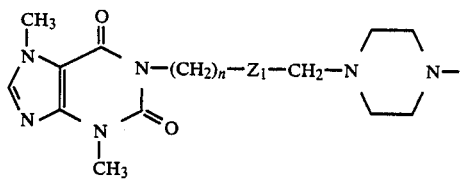
(II)

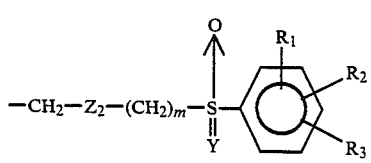

and the pharmaceutically acceptable acid addition salts thereof, wherein

M is selected from the group consisting of hydrogen, morpholino, benzylamino, di-n-lower alkylamino, n-lower alkylamino and

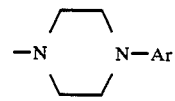

wherein Ar is optionally substituted phenyl;

$Z_1$ and $Z_2$ are each independently selected from the group consisting of $CH_2$, CHOB and C=O, wherein B is selected from the group consisting of hydrogen and alkanoyl;

Y is oxygen or nothing;

n is an integer from 0–4 but cannot be zero when $Z_1$ is CHOB;

m is an integer from 0–4 but cannot be zero when $Z_2$ is CHOB;

$R_1$, $R_2$ and $R_3$ are each independently hydrogen, halogen, hydroxy, trifluoromethyl, alkyl or alkoxy;

$R_4$ is lower alkyl; and $R_5$ is hydrogen or lower alkyl.

In another aspect, this invention concerns pharmaceutical compositions comprising an effective amount of a compound of Formula I or II in combination with at least one pharmaceutically acceptable excipient.

In a third aspect, the invention concerns a method for treating or relieving the symptoms of respiratory and allergic disorders using the above compounds or pharmaceutical compositions containing them.

In a fourth aspect, the invention concerns processes for preparing the compounds of formulas I and II.

DETAILED DESCRIPTION OF THE INVENTION

Definitions

As used herein

"Alkyl" means a branched or unbranched saturated hydrocarbon chain containing 1–6 carbon atoms, such as methyl, ethyl, propyl, tert.-butyl, n-hexyl and the like;

"Lower alkyl" means a branched or unbranched saturated hydrocarbon chain containing 1–4 carbon atoms, such as methyl, ethyl, isopropyl, n-propyl, isobutyl, n-butyl, tert-butyl and the like.

"n-Lower alkylamino" means an amino group which is mono-substituted with an unbranched saturated hydrocarbon chain of 1–4 carbons such as methyl, ethyl, n-propyl, and n-butyl.

"Di-n-lower alkylamino" means an amino group which is di-substituted with two unbranched saturated hydrocarbon chains of 1–4 carbons which are independently chosen from methyl, ethyl, n-propyl and n-butyl.

"Alkoxy" means —OR wherein R is alkyl as herein defined.

"Alkanoyl" means

wherein R is alkyl as defined herein.

"Halogen" means chloro, bromo or iodo.

"Aryl piperazino" is a radical of the formula

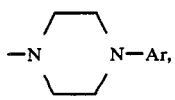

wherein Ar is optionally substituted phenyl.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

"Substituted phenyl" means that one or more hydrogens of the phenyl ring are replaced by moieties selected from the group consisting of lower alkyl, lower alkoxy, halo and trifluoromethyl. In the context of the present invention, said replacement may be at any position of the phenyl ring, and a maximum of 3 hydrogens may be so replaced.

"Pharmaceutically acceptable acid addition salts" refers to those salts which retain the biological effectiveness and properties of the free bases, are not biologically or otherwise undesirable, and are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

Process for Preparation

Reaction Schemes 1 and 2 illustrate processes for preparing the compounds of Formulas I and II.

In the reaction schemes, "R" represents the portion of the compounds of Formulas 1, 2, I and II having the formula:

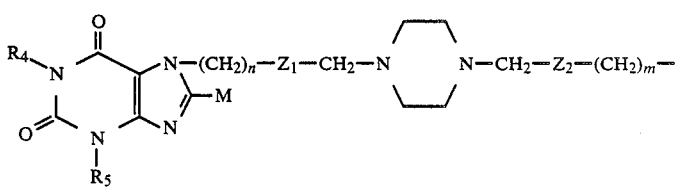

or

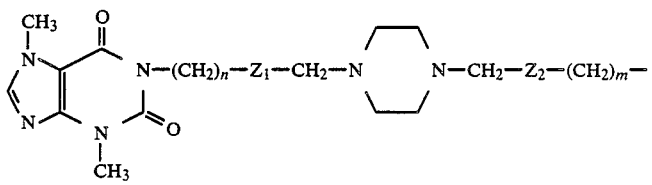

in which M, m, n, $Z_1$, $Z_2$, $R_4$ and $R_5$ have the definitions given hereinabove.

The compounds designated by formulas "1" and "2" are the unoxidized precursors of the corresponding novel compounds of Formulas I and II, respectively, and have the formulas shown below:

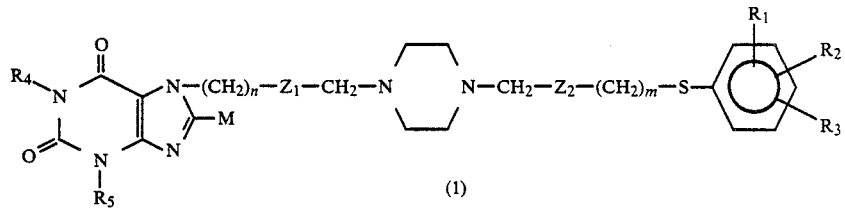

(1)

or

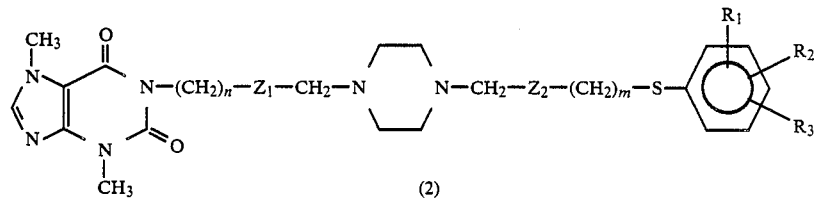

(2)

in which M, m, n, $Z_1$, $Z_2$, $R_1$, $R_2$, $R_3$, $R_4$ and $R_5$ have the definitions given herein.

I. Compounds of the Invention in Which Y is Nothing

The sulfinyl compounds of the invention (those in which Y is nothing) are prepared as shown below in Reaction Scheme 1:

REACTION SCHEME 1

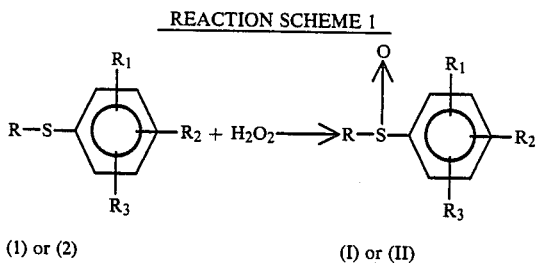

(1) or (2)          (I) or (II)

As shown in Reaction Scheme 1, the sulfinyl compounds of the invention are prepared by oxidation of the corresponding compounds of Formulas 1 or 2. The oxidation takes place by reaction with about 1.1 equivalents of hydrogen peroxide in water, and is performed at a temperature of about 0° C. to 40° C., preferably about 20° C. The reaction mixture is then stirred at room temperature for a period of about 1 to 8, preferably about 4 hours, and the resulting compound of Formula I or II is isolated by conventional means. Methods of preparing the starting compounds of Formulas 1 and 2 are described in detail in U.S. Pat. Nos. 4,374,835, 4,374,837 and 4,400,381, the contents of which are incorporated herein by reference. U.S. Pat. No. 4,374,835 describes the preparation of compounds of Formula 1 in which $R_4$, $R_5$ are each methyl and M is hydrogen. U.S. Pat. No. 4,400,381 describes the preparation of compounds of Formula 1 in which one of $R_4$, $R_5$ and M can be hydrogen or various non-hydrogen substituents. U.S. Pat. No. 4,374,837 describes the preparation of compounds of Formula 2.

II. Compounds of the Invention in Which Y is Oxygen

The sulfonyl compounds of the invention (those in which Y is an oxygen molecule) are prepared as shown below in Reaction Scheme 2:

REACTION SCHEME 2

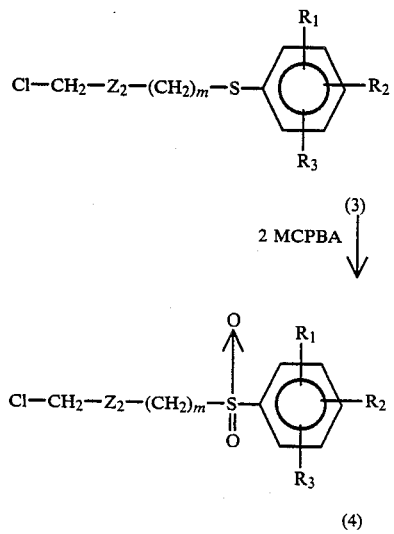

-continued
REACTION SCHEME 2

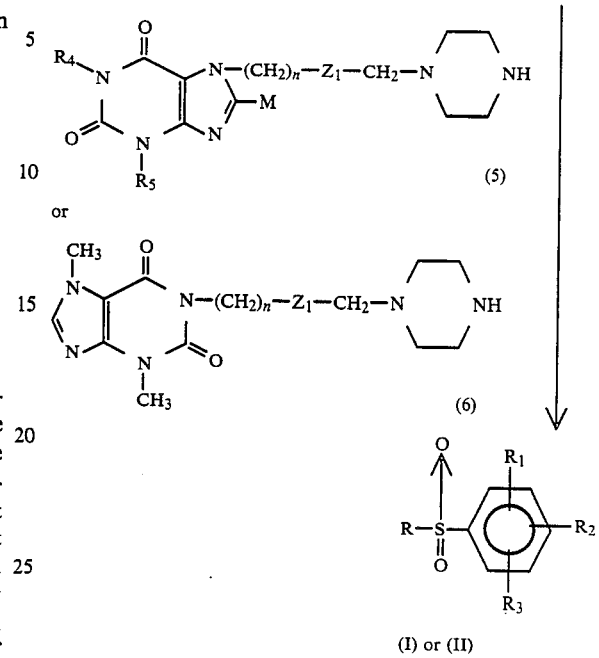

As shown above in Reaction Scheme 2, the sulfonyl compounds of Formulas I and II are prepared by condensation of a compound of Formula 4 with a compound of Formula 5 or 6. The reaction is carried out with approximately equimolar amounts of reactants in the presence of a polar solvent such as for example, aqueous alkanol, a pure polar alcohol, chloroalkane, polar ketone, water, or preferably dimethyl formamide. A basic catalyst such as sodium or potassium hydroxide or carbonate, preferably potassium carbonate, is used, and the reaction is carried out at elevated temperatures of about 50°–120° C., most conveniently at the reflux temperature of the solvent. The reaction is continued for about 12–36 hours, preferably 20–25 hours, and the resulting compound of formula I or II is then isolated by conventional means known to those skilled in the art.

Compounds of Formulas 3, 5 and 6 are prepared as described in U.S. Pat. Nos. 4,374,835, 3,474,837 and 4,400,382, the relevant portions of which are incorporated herein by reference. The compounds of Formula 3 are converted to the corresponding sulfones of Formula 4 by oxidation with approximately 2 molar equivalents of metachloroperbenzoic acid (MCPBA). The reaction is performed in a polar solvent, such as aqueous alkanol, a pure polar alcohol, chloroalkane or chloroketone, preferably chloroform, over a period of about 1 to 5, preferably about 2 hours, at room temperature. The resulting sulfone intermediate of formula 4 is then isolated by conventional means and reacted with an appropriate compound of Formula 5 or 6 to give the corresponding sulfonyl compound of Formula I or II.

Isolation and purification of the final compounds and intermediates shown in the reaction schemes or described in the body of the specification or the examples, can be effected by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other effective separation or isolation procedures can, of course, also be used.

The salt products are also isolated by conventional means. For example, the reaction mixtures may be evaporated to a dryness, and the salts can be further purified by conventional methods.

The compounds of the present invention in which $Z_1$ and/or $Z_2$ is CHOB contain at least one chiral center; these compounds may be prepared in either optically active form or as racemic mixtures. Unless otherwise specified, the compounds described herein are all in the racemic form. However, the scope of the subject invention described and claimed encompasses the individual optical isomers as well as the racemic forms of the compounds of Formulas I and II.

If desired, the compounds of the invention may be resolved into their optical antipodes by conventional resolution means; for example by separation (e.g. fractional crystallization) of the diastereomeric salts formed by the reaction of these compounds with optically active acids. Exemplary of such optically active acids are the optically active forms of camphor-10-sulfonic acid, 2-bromo-camphor-sulfonic acid, camphoric acid, menthoxyacetic acid, tartaric acid, malic acid, diacetyltartaric acid, pyrrolidine-5-carboxylic acid and the like. The separated pure diastereomeric salts may then be cleaved by standard means to afford the respective optical isomers of the compounds of Formula I and II.

The reaction schemes shown offer methods to prepare all of the compounds of the present invention. In addition, compounds of Formulas I and II wherein $Z_1$ and/or $Z_2$ is C=O may be reduced to the corresponding alcohols of Formula I using a metal hydride such as $KBH_4$ or $NaBH_4$ in a polar solvent such as aqueous methanol. The reduction is accomplished by dissolving the substrate carbonyl in the solvent chosen, and adding an excess (the amount of excess depending on the side reaction with solvent) of the hydride in small portions with stirring until reaction is complete. The temperature is kept at about 0°–25° C., preferably 4°–15° C.

Conversely, compounds of Formulas I and II wherein $Z_1$ and/or $Z_2$ is CHOH may be oxidized to the corresponding carbonyls under suitable mild conditions. Appropriate oxidizing agents include, for example, dilute neutral permanganate or chromic acid, preferably permanganate. The substrate alcohol is dissolved in a polar solvent such as water, acetone, MEK, or acetic acid, and a solution of the oxidizing agent added until reaction is complete. In some cases, the reaction may alternatively be conducted with an aprotic solvent such as dichloromethane. Approximately stoichiometric amounts of oxidizing agent are required. The temperature is kept at about 5°–30° preferably 15°–20° C.

Compounds of Formulas I and II wherein $Z_1$ and/or $Z_2$ is CHOH may be esterified to the corresponding alkanoyl derivatives. This is accomplished by heating the compound of Formula I or II with a molar excess of the appropriate carboxylic anhydride or chloride in a tertiary amine solvent, such as, for example, pyridine. The temperature is kept at about 20°–90°, preferably 15°–30°.

Conversely, the compounds of Formulas I and II wherein $Z_1$ and/or $Z_2$ is CHOOCR may be hydrolyzed to the corresponding alcohols using conventional methods well known to those in the art. The ester is heated in a water solution with an acid or basic catalyst until hydrolysis is complete.

Salts of the compounds of Formulas I and II are prepared by reacting the corresponding free bases with appropriate acids or acid salts at a temperature of between 0° and 100° C. Conversely, free bases can be prepared by reacting corresponding acid addition salts with suitable alkaline agents, such as sodium or potassium hydroxide at 0°–100° C.

The products of Formula I, synthesized by any of the pathways described above, are optionally converted to the free base, or any salt, including, but not being limited to the pharmaceutically acceptable acid addition salts.

PREFERRED EMBODIMENTS

Preferred embodiments of the compounds of this invention are those wherein n and m are 1, $Z_1$ and and $Z_2$ are CHOH or $CH_2$, $R_5$ is lower alkyl and at least one of $R_1$, $R_2$ and $R_3$ is hydrogen, and the pharmaceutically acceptable acid addition salts thereof.

More preferred are those embodiments wherein $Z_1$ and $Z_2$ are each independently $CH_2$ or CHOH, M is hydrogen, at least one of $R_4$ and $R_5$ is methyl and at least two of $R_1$, $R_2$ and $R_3$ are hydrogen.

Of these, particularly preferred are the compounds of Formulas I wherein n and m are both 1, $Z_1$ and $Z_2$ are CHOH or $CH_2$; $R_1$, $R_2$ and $R_3$ are each hydrogen, $R_4$ and $R_5$ are both methyl and the pharmaceutically acceptable acid addition salts thereof.

Most preferred are:

1-[3-(1,3-dimethyl-3,7-dihydro-1H-purine-2,6-dion-7-yl)-2-hydroxypropyl]-4-(3-phenylsulfinylpropyl)piperazine; and 1-[3-(1,3-dimethyl-3,7-dihydro-1H-purine-2,6-dion-7-yl)-2-hydroxypropyl]-4-(3-phenylsulfonylpropyl)piperazine.

Utility and Administration

The compounds of the present invention are particularly effective antihistamines. They have been demonstrated to antagonize the effects of histamine in a variety of tests related to such activity, including prevention of anaphylactic shock in rats, bronchodilation in guinea pigs, inhibition of muscle contraction in response to stress in rats, and brachycardial effects in guinea pigs. Additionally, the compounds of this invention have long durations of action in vivo, generally in the range of 16–24 hours. Therefore, the compounds are particularly useful in the treatment of respiratory diseases and allergic reactions in mammals, including, but not limited to, asthma, hay fever, and the common cold. The compounds of Formulas I and II are also capable of topical application and are thus useful in the treatment of allergic dermatosis conditions such as pruritis and other allergic skin disorders.

Administration of the active compounds and salts described herein can be via any of the accepted modes of administration for antihistaminic agents which relieve congestion or otherwise effect the control of allergic or other respiratory symptoms. These methods include oral, parenteral and otherwise systemic, or aerosol forms. Depending on the intended mode, the compositions may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula I or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician. However, an effective dosage is in the range of 1 µg to 1 mg/kg/day, preferably 5–500 µg/kg/day. For an average 70 kg human, this would amount to 70 µg to 70 mg per day, or preferably 350 µg to 70 mg per day.

Typical compositions contain 0.01–95% by weight of active ingredient, with the balance one or more acceptable non-toxic carriers. The percentage of active ingredient, will, of course, depend upon the dosage form and the mode of administration.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound(s) in an amount effective to alleviate the symptoms of the subject being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 2%–95% active ingredient, preferably 5–25%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs a controlled release or sustained-release drug delivery system, such that a constant level of dosage is maintained. Examples include sustained release implants, liquid infusion pumps, oral sustained release dosage forms and the like.

For systemic administration via suppository, traditional binders and carriers include, e.g. polyalkalene glycols or triglycerides. Such suppositories may be formed from mixtures containing active ingredient in the range of 0.1%–10%; preferably 0.5 to 2%.

For aerosol administration, the active ingredient is preferably supplied in finely divided form along with a surfactant and a propellant. Typical percentages of active ingredients are 0.01 to 20% by weight, preferably 0.04 to 1.0%.

Surfactants must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olestearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the trademark "Spans") and the polyoxyethylene and polyoxypropylene derivatives of these esters. Mixed esters, such as mixed or natural glycerides may be employed. The preferred surface-active agents are the oleates or sorbitan, e.g., those sold under the trademarks "Arlacel C" (Sorbitan sesquioleate), "Span 80" (sorbitan monooleate) and "Span 85" (sorbitan trioleate). The surfactant may constitute 0.1–20% by weight of the composition, preferably 0.25–5%.

The balance of the composition is ordinarily propellant. Liquefied propellants are typically gases at ambient conditions, and are condensed under pressure. Among suitable liquefied propellants are the lower alkanes containing up to five carbons, such as butane and propane; and preferably fluorinated or fluorochlorinated alkanes, such as are sold under the trademark "Freon." Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

PREPARATIONS AND EXAMPLES

The following Preparations and Examples are illustrative of the invention, but are not to be construed as limiting it:

PREPARATION I

3-Phenylsulfonyl-1-chloropropane and related compounds of Formula 4

A. 3-Phenylsulfonyl-1-chloropropane 0.1 Mole (18.6 g) 3-phenylthio-1-chloropropane is dissolved in chloroform and reacted with 2 molar equivalents of metachloroperbenzoic acid (MCPBA) at room temperature for 2 hours. The benzoic acid formed by the reaction is removed by filtration; the chloroformic solution is washed with sodium carbonate in water, dried, and evaporated under vacuum to give 3-phenylsulfonyl-1-chloropropane as an oil, characterized by:

RMN 60 MHZ in CCL$_4$ (reference: tetramethylsilane):
8 ppm mult. 2H aromatics 3,5;
7.6 ppm mult. 3H aromatics 2,4,6;
3.5 ppm tripl. 2H CH$_2$Cl;
3.2 ppm tripl. 2H Ph-SO$_2$$\overline{CH_2}$-CH$_2$ B. In a similar manner, but starting instead with other appropriate compounds of Formula 3, the following compounds of Formula 4 are prepared:
3-phenylsulfonyl-1-chloro-2-hydroxypropane;
3-(4-chlorophenyl)sulfonyl-1-chloropropane;
3-(4-chlorophenyl)sulfonyl-1-chloro-2-hydroxypropane;
3-(3-methylphenyl)sulfonyl-1-chloropropane;
3-(3-methylphenyl)sulfonyl-1-chloro-2-hydroxypropane;
3-(4-methoxyphenyl)sulfonyl-1-chloropropane;
3-(4-methoxyphenyl)sulfonyl-1-chloro-2-hydroxypropane;
3-(4-methylphenyl)sulfonyl-1-chloropropane;
3-(4-methylphenyl)sulfonyl-1-chloro-2-hydroxypropane;
3-(4-chloro-3,5-dimethylphenyl)sulfonyl-1-chloropropane;
3-(4-chloro-3,5-dimethylphenyl)sulfonyl-1-chloro-2-hydroxypropane;
3-(2,6-dimethylphenyl)sulfonyl-1-chloropropane;
3-(2,6-dimethylphenyl)sulfonyl-1-chloro-2-hydroxypropane;
3-(3,4,5-trimethoxyphenyl)sulfonyl-1-chloropropane;
3-(3,4,5-trimethoxyphenyl)sulfonyl-1-chloro-2-hydroxypropane;
3-(4-trifluoromethylphenyl)sulfonyl-1-chloropropane;
3-(4-trifluoromethylphenyl)sulfonyl-1-chloro-2-hydroxypropane;
3-(4-ethylphenyl)sulfonyl-1-chloropropane;
3-(4-ethylphenyl)sulfonyl-1-chloro-2-hydroxypropane;
3-(4-bromophenyl)sulfonyl-1-chloropropane;
3-(4-bromophenyl)sulfonyl-1-chloro-2-hydroxypropane;
4-(4-chlorophenyl)sulfonyl-1-chlorobutane;
4-(4-chlorophenyl)sulfonyl-1-chloro-2-hydroxybutane;
2-(3-methylphenyl)sulfonyl-1-chloroethane;
5-(3-methylphenyl)sulfonyl-1-chloro-2-hydroxypentane;
6-(4-methoxyphenyl)sulfonyl-1-chlorohexane; and
6-(4-methoxyphenyl)sulfonyl-1-chloro-2-hydroxyhexane;

EXAMPLE I

1-[3-(1,3-Dimethyl-3,7-dihydro-1H-purine-2,6-dion-7-yl)-2-hydroxypropyl]-4-(3-phenylsulfinylpropyl)piperazine and Related Compounds of Formulas I and II A. 0.1 Moles of 1-[3-(1,3-dimethyl-3,7-dihydro-1H-purine-2,6-dion-7-yl)-2-hydroxypropyl]-4-(3-phenylthio-propyl)piperazine hydrochloride was dissolved in 200 ml demineralized water and maintained at 20° C. 120 ml hydrogen peroxide in 250 ml water was added dropwise. The mixture was stirred for four hours at room temperature. Completion of the reaction was checked by TLC using a mixture of 80/20/1 CH$_2$Cl$_2$/methanol/NH$_4$OH as eluent. When the reaction was completed, the reactive mixture was alkalinized, extracted with methylene chloride, washed with water, dried, and the solvent evaporated under vacuum to give the free base form of 1-[3-(1,3-dimethyl-3,7-dihydro-1H-purine-2,6-dion-7-yl)-2-hydroxypropyl]-4-(3-phenylsulfinylpropyl)piperazine. The dihydrochloride salt was prepared in the manner indicated in Example III, m.p. 260°-265° C.

B. In a similar manner, but starting instead with other appropriate compounds of Formula 1, the following compounds of Formula I are prepared:
1-[3-(1,3-dimethyl-3,7-dihydro-1H-purine-2,6-dion-7-yl)-2-hydroxypropyl]-4-(3-phenylsulfinyl-2-hydroxypropyl)piperazine;
1-[3-(1,3-dimethyl-3,7-dihydro-1H-purine-2,6-dion-7-yl)-2-hydroxypropyl]-4-(3-(4-chlorophenyl)sulfinylpropyl)piperazine;
1-[3-(1,3-dimethyl-3,7-dihydro-1H-purine-2,6-dion-7-yl)-2-hydroxypropyl]-4-(3-(4-chlorophenyl)sulfinyl-2-hydroxypropyl)-piperazine;
1-[3-(1,3-dimethyl-3,7-dihydro-1H-purine-2,6-dion-7-yl)-2-hydroxypropyl]-4-(3-(3-methylphenyl)sulfinylpropyl)piperazine;
1-[3-(1,3-dimethyl-3,7-dihydro-1H-purine-2,6-dion-7-yl)-2-hydroxypropyl]-4-(3-(3-methylphenyl)sulfinyl-2-hydroxypropyl)-piperazine;
1-[3-(1,3-dimethyl-3,7-dihydro-1H-purine-2,6-dion-7-yl)-2-hydroxypropyl]-4-(3-(4-methoxyphenyl)sulfinylpropyl)piperazine;
1-[3-(1,3-dimethyl-3,7-dihydro-1H-purine-2,6-dion-7-yl)-2-hydroxypropyl]-4-(3-(4-methoxyphenyl)sulfinyl-2-hydroxypropyl)piperazine;
1-[3-(3-i-propyl-1-methyl-3,7-dihydro-1H-purine-2,6-dion-7-yl)-2-hydroxypropyl]-4-(3-(4-methylphenyl)-sulfinylpropyl)piperazine;
1-[3-(3-i-propyl-1-methyl-3,7-dihydro-1H-purine-2,6-dion-7-yl)-2-hydroxypropyl]-4-(3-(4-methylphenyl)-sulfinyl-2-hydroxypropyl)piperazine;
1-[3-(3-i-butyl-1-methyl-3,7-dihydro-1H-purine-2,6-dion-7-yl)-2-hydroxypropyl]-4-(3-(4-chloro-3,5-dimethylphenyl)sulfinylpropyl)piperazine;
1-[3-(3-i-butyl-1-methyl-3,7-dihydro-1H-purine-2,6-dion-7-yl)-2-hydroxypropyl]-4-(3-(4-chloro-3,5-dimethylphenyl)-sulfinyl-2-hydroxypropyl)piperazine;
1-[3-(3-n-propyl-1-methyl-3,7-dihydro-1H-purine-2,6-dion-7-yl)-2-hydroxypropyl]-4-(3-(2,6-dimethylphenyl)sulfinyl-propyl)piperazine;
1-[3-(3-n-propyl-1-methyl-3,7-dihydro-1H-purine-2,6-dion-7-yl)-2-hydroxypropyl]-4-(3-(2,6-dimethylphenyl)sulfinyl-2-hydroxypropyl)piperazine;
1-[3-(3-n-butyl-1-methyl-3,7-dihydro-1H-purine-2,6-dion-7-yl)-2-hydroxypropyl]-4-(3-(3,4,5-trimethoxyphenyl)sulfinylpropyl)piperazine;
1-[3-(3-n-butyl-1-methyl-3,7-dihydro-1H-purine-2,6-dion-7-yl)-2-hydroxypropyl]-4-(3-(3,4,5-trimethoxyphenyl)sulfinyl-2-hydroxypropyl)piperazine;
1-[3-(1,3-dimethyl-3,7-dihydro-1H-purine-2,6-dion-7-yl)-2-hydroxypropyl]-4-(3-(4-trifluoromethylphenyl)-sulfinyl-propyl)piperazine;
1-[3-(1,3-dimethyl-3,7-dihydro-1H-purine-2,6-dion-7-yl)propyl]-4-(3-(4-trifluoromethylphenyl)sulfinyl-2-hydroxypropyl)piperazine;
1-[3-(1,3-dimethyl-3,7-dihydro-1H-purine-2,6-dion-7-yl)-2-hydroxypropyl]-4-(3-(4-ethylphenyl)sulfinylpropyl)piperazine;
1-[3-(1,3-dimethyl-3,7-dihydro-1H-purine-2,6-dion-7-yl)propyl]-4-(3-(4-ethylphenyl)sulfinyl-2-hydroxypropyl)piperazine;
1-[3-(1,3-dimethyl-3,7-dihydro-1H-purine-2,6-dion-7-yl)-2-hydroxypropyl]-4-(3-(4-bromophenyl)sulfinylpropyl)piperazine;

1-[3-(1,3-dimethyl-3,7-dihydro-1H-purine-2,6-dion-7-yl)propyl]-4-(3-(4-bromophenyl)sulfinyl-2-hydroxypropyl)piperazine;

1-[3-(1,3-dimethyl-3,7-dihydro-1H-purine-2,6-dion-7-yl)-2-hydroxypropyl]-4-(4-(4-chlorophenyl)sulfinylbutyl)piperazine;

1-[3-(1,3-dimethyl-3,7-dihydro-1H-purine-2,6-dion-7-yl)propyl]-4-(4-(4-chlorophenyl)sulfinyl-2-hydroxybutyl)piperazine;

1-[3-(1,3-dimethyl-3,7-dihydro-1H-purine-2,6-dion-7-yl)-2-hydroxypropyl]-4-(2-(3-methylphenyl)sulfinylethyl)piperazine;

1-[3-(1,3-dimethyl-3,7-dihydro-1H-purine-2,6-dion-7-yl)propyl]-4-(5-(3-methylphenyl)sulfinyl-2-hydroxypentyl)piperazine;

1-[3-(1,3-dimethyl-3,7-dihydro-1H-purine-2,6-dion-7-yl)-2-hydroxypropyl]-4-(6-(4-methoxyphenyl)sulfinylhexyl)piperazine;

1-[3-(1,3-dimethyl-3,7-dihydro-1H-purine-2,6-dion-7-yl)propyl]-4-(6-(4-methoxyphenyl)sulfinyl-2-hydroxyhexyl)piperazine;

1-[3-(8-morpholino-3-i-butyl-1-methyl-3,7-dihydro-1H-purine-2,6-dion-7-yl)-2-hydroxypropyl]-4-(3-phenylsulfinylpropyl)piperazine;

1-[3-(8-morpholino-1,3-dimethyl-3,7-dihydro-1H-purine-2,6-dion-7-yl)-2-hydroxypropyl]-4-(3-(4-phenylsulfinylpropyl)piperazine;

1-[3-(8-morpholino-1,3-dimethyl-3,7-dihydro-1H-purine-2,6-dion-7-yl)-2-hydroxypropyl]-4-(3-(4-methylphenyl)sulfinylpropyl)piperazine;

1-[3-(8-morpholino-3-n-butyl-1-methyl-3,7-dihydro-1H-purine-2,6-dion-7-yl)-2-hydroxypropyl]-4-(3-phenylsulfinylpropyl)piperazine;

1-[3-(8-di-n-butylamino-3,7-dihydro-1H-purine-2,6-dion-7-yl)-2-hydroxypropyl]-4-(3-(4-methylphenyl)-sulfinylpropyl)piperazine;

1-[3-(8-di-n-butylamino-1,3-dimethyl-3,7-dihydro-1H-purine-2,6-dion-7-yl)-2-hydroxypropyl]-4-(3-phenylsulfinyl-2-hydroxypropyl)piperazine;

1-[3-(8-benzylamino-1,3-dimethyl-3,7-dihydro-1H-purine-2,6-dion-7-yl)propyl]-4-(6-phenylsulfinyl-2-hydroxyhexyl)piperazine; and 1-[3-(8-(1-(2-methoxyphenyl)piperazin-4-yl)-1,3-dimethyl-3,7-dihydro-1H-purine-2,6-dion-7-yl)-2-hydroxypropyl]-4-(3-phenylsulfinylpropyl)piperazine.

C. Similarly, but starting instead with appropriate compounds of Formula 2, the following compounds of Formula II are prepared:

1-(3-theobromin-1-yl-2-hydroxypropyl)-4-(3-phenylsulfinylpropyl)piperazine;

1-(3-theobromin-1-yl-propyl)-4-(3-phenylsulfinylpropyl)piperazine;

1-(3-theobromin-1-yl-2-hydroxypropyl)-4-(3-(4-chlorophenyl)sulfinylpropyl)piperazine;

1-(3-theobromin-1-yl-propyl)-4-(3-(4-chlorophenyl)sulfinylpropyl)piperazine;

1-(3-theobromin-1-yl-2-hydroxypropyl)-4-(3-(4-methoxyphenyl)sulfinylpropyl)piperazine;

1-(3-theobromin-1-yl-propyl)-4-(3-(4-methoxyphenyl)sulfinylpropyl)piperazine;

1-(3-theobromin-1-yl-2-hydroxypropyl)-4-(3-(4-methylphenyl)sulfinylpropyl)piperazine;

1-(3-theobromin-1-yl-propyl)-4-(3-(4-methylphenyl)sulfinylpropyl)piperazine;

1-(3-theobromin-1-yl-2-hydroxypropyl)-4-(3-(4-chloro-3,5-dimethylphenyl)sulfinylpropyl)piperazine;

1-(3-theobromin-1-yl-propyl)-4-(3-(4-chloro-3,5-dimethylphenyl)sulfinylpropyl)piperazine;

1-(3-theobromin-1-yl-propyl)-4-(3-(2,6-dimethylphenyl)sulfinylpropyl)piperazine;

1-(3-theobromin-1-yl-propyl)-4-(3-(2,6-dimethylphenyl)sulfinyl-2-hydroxypropyl)piperazine;

1-(3-theobromin-1-yl-2-hydroxypropyl)-4-(3-(3,4,5-trimethoxyphenyl)sulfinylpropyl)piperazine;

1-(3-theobromin-1-yl-2-hydroxypropyl)-4-(3-(3,4,5-trimethoxyphenyl)sulfinyl-2-hydroxypropyl)piperazine;

1-(3-theobromin-1-yl-2-hydroxypropyl)-4-(3-(4-trifluoromethylphenyl)sulfinylpropyl)piperazine;

1-(3-theobromin-1-yl-2-hydroxypropyl)-4-(3-(4-trifluoromethylphenyl)sulfinyl-2-hydroxypropyl)piperazine;

1-(3-theobromin-1-yl-2-hydroxypropyl)-4-(3-(4-ethylphenyl)sulfinylpropyl)piperazine;

1-(3-theobromin-1-yl-2-hydroxypropyl)-4-(3-(4-ethylphenyl)sulfinyl-2-hydroxypropyl)piperazine;

1-(3-theobromin-1-yl-2-hydroxypropyl)-4-(3-(4-bromophenyl)sulfinylpropyl)piperazine;

1-(3-theobromin-1-yl-2-hydroxypropyl)-4-(3-(4-bromophenyl)sulfinyl-2-hydroxypropyl)piperazine;

1-(3-theobromin-1-yl-2-hydroxypropyl)-4-(4-(4-chlorophenyl)sulfinylbutyl)piperazine;

1-(3-theobromin-1-yl-2-hydroxypropyl)-4-(4-(4-chlorophenyl)sulfinyl-2-hydroxybutylpiperazine;

1-(3-theobromin-1-yl-2-hydroxypropyl)-4-(2-(3-methylphenyl)sulfinylethyl)piperazine;

1-(3-theobromin-1-yl-2-hydroxypropyl)-4-(5-(3-methylphenyl)sulfinyl-2-hydroxypentyl)piperazine;

1-(3-theobromin-1-yl-2-hydroxypropyl)-4-(6-(4-methoxyphenyl)sulfinylhexyl)piperazine;

EXAMPLE II

1-[3-(1,3-Dimethyl-3,7-dihydro-1H-purine-2,6-dion-7-yl)-2-hydroxypropyl]-4-(3-phenylsulfonylpropyl)piperazine and Related Compounds of Formulas I and II A. 0.13 Moles of 3-phenylsulfonyl-1-chloropropane were combined with 0.14 moles of 1-[3-(1,3-dimethyl-3,7-dihydro-1H-purine-2,6-dion-7-yl)-2-hydroxypropyl]piperazine dihydrochloride and 0.3 moles potassium carbonate in 600 grams dimethylformamide. The mixture was stirred overnight at 60° C. After cooling, the reaction mixture was poured into water, extracted with CH$_2$Cl$_2$, washed with water, dried, and evaporated with gentle heating. The residue was recrystallized from ethanol to give the free base form of 1-[3-(1,3-Dimethyl-3,7-dihydro-1H-purine-2,6-dion-7-yl)-2-hydroxypropyl]-4-(3-phenylsulfonylpropyl)piperazine, m.p. 168° C. The dihydrochloride was obtained by adjunction with 12N hydrogen chloride solution as described in Example III, m.p. 190° C.

B. In a similar manner, but replacing the 3-phenylsulfonyl-1-chloropropane as needed with other appropriate compounds of Formula 4, the preparation of which is described in Preparation 1, and optionally substituting for the 1-[3-(1,3-dimethyl-3,7-dihydro-1H-purine-2,6-dion-7-yl)-2-hydroxypropyl]piperazine other appropriate compounds of Formula 5, the following compounds of Formula I are obtained:

1-[3-(1,3-dimethyl-3,7-dihydro-1H-purine-2,6-dion-7-yl)-2-hydroxypropyl]-4-(3-phenylsulfonyl-2-hydroxypropyl)piperazine;

1-[3-(1,3-dimethyl-3,7-dihydro-1H-purine-2,6-dion-7-yl)-2-hydroxypropyl]-4-(3-(4-chlorophenyl)sulfonylpropyl)piperazine;

1-[3-(1,3-dimethyl-3,7-dihydro-1H-purine-2,6-dion-7-yl)-2-hydroxypropyl]-4-(3-(4-chlorophenyl)sulfonyl-2-hydroxypropyl)-piperazine;

1-[3-(1,3-dimethyl-3,7-dihydro-1H-purine-2,6-dion-7-yl)-2-hydroxypropyl]-4-(3-(3-methylphenyl)sulfonylpropyl)piperazine;

1-[3-(1,3-dimethyl-3,7-dihydro-1H-purine-2,6-dion-7-yl)-2-hydroxypropyl]-4-(3-(3-methylphenyl)sulfonyl-2-hydroxypropyl)-piperazine;

1-[3-(1,3-dimethyl-3,7-dihydro-1H-purine-2,6-dion-7-yl)-2-hydroxypropyl]-4-(3-(4-methoxyphenyl)sulfonylpropyl)piperazine;

1-[3-(1,3-dimethyl-3,7-dihydro-1H-purine-2,6-dion-7-yl)-2-hydroxypropyl]-4-(3-(4-methoxyphenyl)sulfonyl-2-hydroxypropyl)piperazine;

1-[3-(3-i-propyl-1-methyl-3,7-dihydro-1H-purine-2,6-dion-7-yl)-2-hydroxypropyl]-4-(3-(4-methylphenyl)-sulfonylpropyl)piperazine;

1-[3-(3-i-propyl-1-methyl-3,7-dihydro-1H-purine-2,6-dion-7-yl)-2-hydroxypropyl]-4-(3-(4-methylphenyl)-sulfonyl-2-hydroxypropyl)piperazine;

1-[3-(3-i-butyl-1-methyl-3,7-dihydro-1H-purine-2,6-dion-7-yl)-2-hydroxypropyl]-4-(3-(4-chloro-3,5-dimethylphenyl)sulfonylpropyl)piperazine;

1-[3-(3-i-butyl-1-methyl-3,7-dihydro-1H-purine-2,6-dion-7-yl)-2-hydroxypropyl]-4-(3-(4-chloro-3,5-dimethylphenyl)-sulfonyl-2-hydroxypropyl)piperazine;

1-[3-(3-n-propyl-1-methyl-3,7-dihydro-1H-purine-2,6-dion-7-yl)-2-hydroxypropyl]-4-(3-(2,6-dimethylphenyl)sulfonyl-propyl)piperazine;

1-[3-(3-n-propyl-1-methyl-3,7-dihydro-1H-purine-2,6-dion-7-yl)-2-hydroxypropyl]-4-(3-(2,6-dimethylphenyl)sulfonyl-2-hydroxypropyl)piperazine;

1-[3-(3-n-butyl-1-methyl-3,7-dihydro-1H-purine-2,6-dion-7-yl)-2-hydroxypropyl]-4-(3-(3,4,5-trimethoxyphenyl)sulfonylpropyl)piperazine;

1-[3-(3-n-butyl-1-methyl-3,7-dihydro-1H-purine-2,6-dion-7-yl)-2-hydroxypropyl]-4-(3-(3,4,5-trimethoxyphenyl)sulfonyl-2-hydroxypropyl)piperazine;

1-[3-(1,3-dimethyl-3,7-dihydro-1H-purine-2,6-dion-7-yl)-2-hydroxypropyl]-4-(3-(4-trifluoromethylphenyl)-sulfonyl-propyl)piperazine;

1-[3-(1,3-dimethyl-3,7-dihydro-1H-purine-2,6-dion-7-yl)propyl]-4-(3-(4-trifluoromethylphenyl)sulfonyl-2-hydroxypropyl)piperazine;

1-[3-(1,3-dimethyl-3,7-dihydro-1H-purine-2,6-dion-7-yl)-2-hydroxypropyl]-4-(3-(4-ethylphenyl)sulfonylpropyl)piperazine;

1-[3-(1,3-dimethyl-3,7-dihydro-1H-purine-2,6-dion-7-yl)propyl]-4-(3-(4-ethylphenyl)sulfonyl-2-hydroxypropyl)piperazine;

1-[3-(1,3-dimethyl-3,7-dihydro-1H-purine-2,6-dion-7-yl)-2-hydroxypropyl]-4-(3-(4-bromophenyl)sulfonylpropyl)piperazine;

1-[3-(1,3-dimethyl-3,7-dihydro-1H-purine-2,6-dion-7-yl)propyl]-4-(3-(4-bromophenyl)sulfonyl-2-hydroxypropyl)piperazine;

1-[3-(1,3-dimethyl-3,7-dihydro-1H-purine-2,6-dion-7-yl)-2-hydroxypropyl]-4-(4-(4-chlorophenyl)sulfonylbutyl)piperazine;

1-[3-(1,3-dimethyl-3,7-dihydro-1H-purine-2,6-dion-7-yl)propyl]-4-(4-(4-chlorophenyl)sulfonyl-2-hydroxybutyl)piperazine;

1-[3-(1,3-dimethyl-3,7-dihydro-1H-purine-2,6-dion-7-yl)-2-hydroxypropyl]-4-(2-(3-methylphenyl)sulfonylethyl)piperazine;

1-[3-(1,3-dimethyl-3,7-dihydro-1H-purine-2,6-dion-7-yl)propyl]-4-(5-(3-methylphenyl)sulfonyl-2-hydroxypentyl)piperazine;

1-[3-(1,3-dimethyl-3,7-dihydro-1H-purine-2,6-dion-7-yl)-2-hydroxypropyl]-4-(6-(4-methoxyphenyl)sulfonylhexyl)piperazine; and 1-[3-(1,3-dimethyl-3,7-dihydro-1H-purine-2,6-dion-7-yl)propyl]-4-(6-(4-methoxyphenyl)sulfonyl-2-hydroxyhexyl)piperazine.

1-[3-(8-morpholino-3-i-butyl-1-methyl-3,7-dihydro-1H-purine-2,6-dion-7-yl)-2-hydroxypropyl]-4-(3-phenylsulfonylpropyl)piperazine;

1-[3-(8-morpholino-1,3-dimethyl-3,7-dihydro-1H-purine-2,6-dion-7-yl)-2-hydroxypropyl]-4-(3-phenylsulfonylpropyl)piperazine;

1-[3-(8-morpholino-1,3-dimethyl-3,7-dihydro-1H-purine-2,6-dion-7-yl)-2-hydroxypropyl]-4-(3-(4-methylphenyl)sulfonylpropyl)piperazine;

1-[3-(8-morpholino-3-n-butyl-1-methyl-3,7-dihydro-1H-purine-2,6-dion-7-yl)-2-hydroxypropyl]-4-(3-phenylsulfonylpropyl)piperazine;

1-[3-(8-di-n-butylamino-3,7-dihydro-1H-purine-2,6-dion-7-yl)-2-hydroxypropyl]-4-(3-(4-methylphenyl)-sulfonylpropyl)piperazine;

1-[3-(8-di-n-butylamino-1,3-dimethyl-3,7-dihydro-1H-purine-2,6-dion-7-yl)-2-hydroxypropyl]-4-(3-phenylsulfonyl-2-hydroxypropyl)piperazine;

1-[3-(8-benzylamino-1,3-dimethyl-3,7-dihydro-1H-purine-2,6-dion-7-yl)propyl]-4-(6-phenylsulfonyl-2-hydroxyhexyl)piperazine; and 1-[3-(8-(1-(2-methoxyphenyl)piperazin-4-yl)-1,3-dimethyl-3,7-dihydro-1H-purine-2,6-dion-7-yl)-2-hydroxypropyl]-4-(3-phenylsulfonylpropyl)piperazine.

C. Similarily, but starting, if desired, with other appropriate compounds of Formula 4, and replacing the 1-[3-(1,3-dimethyl-3,7-dihydro-1H-purine-2,6-dion-7-yl)-2-hydroxypropyl]piperazine with corresponding compounds of Formula 6, the following compounds of Formula II are prepared:

1-(3-theobromin-1-yl-2-hydroxypropyl)-4-(3-phenylsulfonylpropyl)piperazine;

1-(3-theobromin-1-yl-propyl)-4-(3-phenylsulfonylpropyl)piperazine;

1-(3-theobromin-1-yl-2-hydroxypropyl)-4-(3-(4-chlorophenyl)sulfonylpropyl)piperazine;

1-(3-theobromin-1-yl-propyl)-4-(3-(4-chlorophenyl)sulfonylpropyl)piperazine;

1-(3-theobromin-1-yl-2-hydroxypropyl)-4-(3-(4-methoxyphenyl)sulfonylpropyl)piperazine;

1-(3-theobromin-1-yl-propyl)-4-(3-(4-methoxyphenyl)-sulfonylpropyl)piperazine;

1-(3-theobromin-1-yl-2-hydroxypropyl)-4-(3-(4-methylphenyl)sulfonylpropyl)piperazine;

1-(3-theobromin-1-yl-propyl)-4-(3-(4-methylphenyl)sulfonylpropyl)piperazine;

1-(3-theobromin-1-yl-2-hydroxypropyl)-4-(3-(4-chloro-3,5-dimethylphenyl)sulfonylpropyl)piperazine;

1-(3-theobromin-1-yl-propyl)-4-(3-(4-chloro-3,5-dimethylphenyl)sulfonylpropyl)piperazine;

1-(3-theobromin-1-yl-propyl)-4-(3-(2,6-dimethylphenyl)sulfonylpropyl)piperazine;

1-(3-theobromin-1-yl-propyl)-4-(3-(2,6-dimethylphenyl)sulfonyl-2-hydroxypropyl)piperazine;

1-(3-theobromin-1-yl-2-hydroxypropyl)-4-(3-(3,4,5-trimethoxyphenyl)sulfonylpropyl)piperazine;

1-(3-theobromin-1-yl-2-hydroxypropyl)-4-(3-(3,4,5-trimethoxyphenyl)sulfonyl-2-hydroxypropyl)piperazine;

1-(3-theobromin-1-yl-2-hydroxypropyl)-4-(3-(4-trifluoromethylphenyl)sulfonylpropyl)piperazine;

1-(3-theobromin-1-yl-2-hydroxypropyl)-4-(3-(4-trifluoromethylphenyl)sulfonyl-2-hydroxypropropyl)piperazine;

1-(3-theobromin-1-yl-2-hydroxypropyl)-4-(3-(4-ethylphenyl)sulfonylpropyl)piperazine;

1-(3-theobromin-1-yl-2-hydroxypropyl)-4-(3-(4-ethylphenyl)sulfonyl-2-hydroxypropyl)piperazine;

1-(3-theobromin-1-yl-2-hydroxypropyl)-4-(3-(4-bromophenyl)sulfonylpropyl)piperazine;

1-(3-theobromin-1-yl-2-hydroxypropyl)-4-(3-(4-bromophenyl)sulfonyl-2-hydroxypropyl)piperazine;

1-(3-theobromin-1-yl-2-hydroxypropyl)-4-(4-(4-chlorophenyl)sulfonylbutyl)piperazine;

1-(3-theobromin-1-yl-2-hydroxypropyl)-4-(4-(4-chlorophenyl)sulfonyl-2-hydroxybutylpiperazine;

1-(3-theobromin-1-yl-2-hydroxypropyl)-4-(2-(3-methylphenyl)sulfonylethyl)piperazine;

1-(3-theobromin-1-yl-2-hydroxypropyl)-4-(5-(3-methylphenyl)sulfonyl-2-hydroxypentyl)piperazine; and 1-(3-theobromin-1-yl-2-hydroxypropyl)-4-(6-(4-methoxyphenyl)sulfonylhexyl)piperazine.

EXAMPLE III

Conversion of free base to salt

Excess 3% hydrogen chloride in methanol is added to a solution of 1.0 g. 1-[3-(1,3-dimethyl-3,7-dihydro-1H-purine-2,6-dion-7-yl)-2-hydroxypropyl]-4-(3-phenylsulfinylpropyl)piperazine in 20 ml methanol. Diethyl ether is added until precipitation is complete. The product dihydrochloride is filtered, washed with ether, air dried and recrystallized, m.p. 260°–265° C.

In a similar manner, all compounds of Formulas I and II in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE IV

Conversion of salt to free acid 1.0 g of 1-[3-(1,3-dimethyl-3,7-dihydro-1H-purine-2,6-dion-7-yl)-2-hydroxypropyl]-4-(3-phenylsulfinylpropyl)piperazine dihydrochloride suspended in 50 ml of ether is stirred with excess dilute aqueous potassium carbonate solution until the salt is completely dissolved. The organic layer is then separated, washed twice with water, dried over magnesium sulfate and evaporated to yield 1-[3-(1,3-dimethyl-3,7-dihydro-1H-purine-2,6-dion-7-yl)-2-hydroxypropyl]-4-(3-phenylsulfinylpropyl)piperazine as the free base.

EXAMPLE V

Conversion of alcohol to ester

A. 1.0 grams of 1-[3-(1,3-dimethyl-3,7-dihydro-1H-purine-2,6-dion-7-yl)-2-hydroxypropyl]-4-(3-phenylsulfinylpropyl)piperazine is dissolved in 30 ml pyridine. 2 ml of acetic anhydride is then added. The mixture kept at room temperature for 20 hours. Solvent is evaporated and the ester 1-[3-(1,3-dimethyl-3,7-dihydro-1H-purine-2,6-dion-7-yl)-2-acetoxypropyl]-4-3-phenylsulfinylpropyl)piperazine, is then isolated, recrystallized by conventional techniques, as the dihydrochloride.

B. In a manner similar to that described in part A of this Example, the corresponding n-propionyloxy, i-butyryloxy, valeryloxy and n-capryloxy compounds, and the like, derived from 1-[3-(1,3-dimethyl-3,7-dihydro-1H-purine-2,6-dion-7-yl)-2-hydroxypropyl]-4-(3-phenylsulfinylpropyl)piperazine, are prepared.

EXAMPLE VI

Pharmaceutical Compositions

The active ingredient in this example is 1-[3-(1,3-dimethyl-3,7-dihydro-1H-purine-2,6-dion-7-yl)-2-hydroxypropyl]-4-(3-phenylsulfonylpropyl)piperazine. The other compounds of this invention may, or course, also be used.

| A. | CAPSULES | |
|---|---|---|
| | Active Ingredient | 30.0 mg |
| | Lactose, special | 163.0 mg |
| | microcrystalline cellulose | 5.0 mg |
| | Magnesium stearate | 2.0 mg |
| B. | INJECTABLE AMPOULES | |
| | Active Ingredient | 10.0 mg |
| | Sodium chloride | 35.0 mg |
| | Monosodium phosphate, to pH 5.5–6 | |
| | Distilled water, qs ad | 5.0 ml |
| C. | TABLETS | |
| | Active Ingredient | 10.0 mg |
| | Lactose | 80.0 mg |
| | Cellulose | 97.5 mg |
| | Silica | 1.5 mg |
| | Starch | 10.0 mg |
| | Magnesium stearate | 1.0 mg |
| D. | DRINKABLE SUSPENSION | |
| | Active Ingredient | 200.0 mg |
| | Benzoic acid | 250.0 mg |
| | Polyoxyethylene glycol and water, qs ad | 200.0 ml |
| E. | AEROSOL I | |
| | Active Ingredient | 0.6% |
| | Span 85 | 0.5% |
| | Freon 11 | 20.0% |
| | Freon 12/Freon 114 (20/80) | 78.9% |
| | AEROSOL II | |
| | Active Ingredient | 0.88% |
| | Sodium sulfate (anhydrous), micronized | 0.88% |
| | Span 85 | 1.00% |
| | Propellant consisting of 50% Freon 12, 25% Freon 11, and 25% Freon 114 | 97.24% |
| | AEROSOL III | |
| | Active Ingredient | 0.50% |
| | Span 80 | 0.50% |
| | Propellant (C) consisting of 30% Freon 11 and 70% Freon W | 99.0% |
| | AEROSOL IV | |
| | Active Ingredient | 3.0% |
| | Span 85 (sorbitan trioleate) | 1.0% |
| | Freon 11 (trichloromonofluoromethane) | 30.0% |
| | Freon 114 (dichlorotetrafluoroethane) | 41.0% |
| | Freon 12 (dichlorodifluoromethane) | 25.0% |

EXAMPLE VII

Antianaphylactic action

The test is effected with male Sprague Dawley rats (IFFA CREDO) weighing 250 g. At time 0, the animals are sensitized with an injection of egg-albumin (1 mg, s.c.) and of aluminum hydroxide (200 mg, s.c.), simultaneously with an injection of *Haemophilus pertussis* vaccine (Vaxicoq ® PASTEUR $1.5 \times 10^{10}$ organisms/0.5 ml, at a rate of 1.5 ml/i.p./rat). After a period of time of 14 days, the rats are anesthetized with ether and a blood sample is obtained by puncturing the descending aorta.

After centrifugation and dilution, the antiserum is reinjected to other male Sprague Dawley rats (180–200 g) by the intradermal route (0.1 ml/i.d.) and on 3 different sites of the dorsal area. After 24 hours, the test material is administered orally, 30 minutes prior to an intradermal histamine injection on three other sites of the dorsal area (30 μg/kg/i.d.) and a simultaneous intravenous injection of a physiological solution containing 5 mg egg-albumin and 2.5 mg Evans Blue (1 ml/rat); after a period of time of 30 minutes, the animals are sacrificed by administration of an overdose of ether; the skin of the back is cut off, turned inside out and the spread out.

Under the influence of the antigen (egg-albumin), the 3 sites corresponding to the prior antiserum (anti-egg-albumin) exhibit a blue color due to the local diffusion of the Evans Blue (histamine release by the subcutaneous mastocytes). The 3 other sites corresponding to the local action of histamine, show the good reactivity of the controls together with the specific antihistaminic action of the test material.

The surface area of each spot is calculated according to the formula:

$$L \times l \times \frac{\pi}{4}$$

in which L and l represent the long and the short axis, respectively, of the ellipse. The best dilution of the reference antiserum correspondings to a surface area of about 100 mm2. The color strength is in turn evaluated according to the following scale:
0: nil
0.5: very pale blue
1: pale blue
1.5: deep blue
2: very deep blue The antianaphylactic action of the product is obtained by averaging the percent inhibition obtained on the surface of the spots and their color strength.

The compounds of the Formula I, and more particularly the compounds of Examples 1, 2, 4, 5, 11, 12, 15, 16 and 17, at single dosages of 10–50 mg, induce an inhibition.

EXAMPLE VIII

Bronchodilator action

Tri-colored male guinea pigs weighing 250–300 g (C.E.R.J. Janvier) are used for the test. The animals are anesthetized with ethyl carbamate (1–2 g/kg/i.p.). A tracheal cannula is positioned and connected to a respiratory pump for small animals (Ideal—Palmer type).

The animals are maintained under forced respiration, at a determined rate and frequency level.

An electromagnetic cell is mounted in line on the blowing circuit; the signal released by this sensor is amplified with a pressure preamplifier and amplifier before being received by a potentiometric recorder.

The brochoconstrictor agents are administered intravenously (jugular vein) after the animals have been allowed to rest for a certain period of time and a gallamine injection (1 mg$\times$kg$^{-1}$/i.v.) in order to prevent, by curarization, the specifically involuntary muscular reactions. After a constant bronchospasm has been obtained, the test material is iteratively administered by the intravenous (or intragastric) route until the reference brochospasm is again obtained. The spasm-inducing agents are histamine (5 μg$\times$kg$^{-1}$/i.v.), serotonine (10 μg$\times$kg$^{-1}$/i.v.) and acetylcholine (20 μg$\times$kg$^{-1}$/i.v.).

The percent inhibition of the reference bronchospasm is a measure of the activity of the test material.

The compounds of the Formula I and more particularly the compounds of Examples 1, 2, 3, 4, 5, 8, 11, 12, 13, 14 and 15, at single dosages of 0.002–2 mg, provide a protection against bronchoconstrictor agents such as histamine, acetyl choline and serotonine.

EXAMPLE IX

Musculoptropic action

The investigation is conducted on the isolated duodenum of rat, with respect to barium chloride-induced contracations.

Male Sprague Dawley rats, weighing 300–400 g and which have been kept fasting for 24 hours are used to test animals.

After decapitation of the animal, a portion of the duodenum (3–4 cm long) is taken and positioned in a test tube for isolated organ containing Tyrode liquid, thermostatically maintained at a temperature of 36.5° C. under an air atmosphere. The other end of the duodenum is connected to an isometric stress guage; at the start, the organ is stretched up to 500 mg. The BaCl$_2$ dosage (about 200 μg$\times$ml$^{-1}$ of bath) is selected in such a manner as to obtain a constant response.

The test material, dissolved in Tyrode liquid, is added at increasing dosages, preventively to the contractions of the organ. The effect of the products is given as percent inhibition of the reference contraction.

The compounds of Formula I are generally effective at dosages between 3 and 60 μg/ml.

EXAMPLE X

Chronotropic action

The investigation is effected on the isolated auricle of guinea pigs. The animals weigh 300–500 g and are sacrificed by decapitation. The right auricle is taken and placed in Tyrode's liquid, under an atmosphere containing 95% O$_2$ and 5% CO$_2$ and thermostatically maintained at 30° C. The auricle is attached to the bottom of the isolated organ cell, and the other end is connected to an isometric gauge.

The auricle beats in a spontaneous manner (automaticity of the pace-maker cells of the nodal tissue) and the cardiac frequency is recorded from the signals released by the sensor, amplified and integrated via a cardiotachymeter. The test materials, dissolved in Tyrode's liquid, are generally administered cumulatively until a maximum effect is produced.

The compounds of the Formula I, and more particularly the compounds of Examples, 1, 2, 3, 4, 5, 8, 11, 12, 13, 14, 15 and 16 have a negative chronotropic effect (bradycardia), while theophylline has a positive chronotropic action (tachycardia).

EXAMPLE XI

Toxicity

Male Sprague Dawley rats (IFFA CREDO France) weighing about 150 g are used as test animals. The animals are fasted the day prior to the test.

On the day of the treatment, they are orally administered a single dose of product suspended in gum water containing 3% gum arabic. The animals are then observed in individual cages to detect the disorders induced by the toxic action of the product; the deaths which may occur are recorded for a period of time of 14 days. The oral toxicity of compounds of Formulas I and II is 500 to 2000 mg/kg in rats.

We claim:

1. A compound named as 1-[3-(1,3-dimethyl-3,7-dihydro-1H-purine-2,6-dion-7-yl)-2-hydroxypropyl]-4-(3-phenylsulfinylpropyl)piperazine, and the pharmaceutically acceptable acid addition salts thereof.

2. A pharmaceutical composition for use as an antihistaminic agent which comprises an effective amount of a compound of claim 1 in combination with at least one pharmaceutically acceptable excipient.

3. A method of treating or relieving the symptoms of respiratory and allergic disorders by administering to a mammal in need of such treatment or relief an effective amount of a compound of claim 1.

* * * * *